US00PP08292P

United States Patent [19]

VandenBerg

[11] Patent Number: Plant 8,292

[45] Date of Patent: Jul. 6, 1993

[54] CHRYSANTHEMUM PLANT NAMED REGAL DAVIS

[75] Inventor: Cornelis P. VandenBerg, Salinas, Calif.

[73] Assignee: Yoder Brothers, Inc., Barberton, Ohio

[21] Appl. No.: 737,984

[22] Filed: Jul. 30, 1991

[51] Int. Cl.[5] ..... A01H 5/00

[52] U.S. Cl. ..... Plt./74.1

[58] Field of Search ..... Plt./74.1

[56] References Cited

U.S. PATENT DOCUMENTS 4,616,099 10/1986 Sparkes ..... 47/58

OTHER PUBLICATIONS

Gosling, ed., 1979, "The Chrysanthemum manual-6th edition", The National Chrysanthemum Society, London, Essex Telegraph Press, Ltd., pp. 329-336.

Broertjes, et ala., 1978, "Application of Mutation Breeding Methods in the Improvement of Vegetatively Propagated Crops", Elsevier Sci. Pub. Co., New York, pp. 162-175.

Broertjes, et al., 1980, "A mutant of a mutant of a . . . Irradiation of progressive radiation-induced mutants in mutation breeding programme with *C. morifilium*", Euphytica, 29:526-530.

Searly, et al., 1968, "Chrysanthemums the Year Round", Blanford Press, London, pp. 27-29, 320-327.

Chan, 1966, "Chrysanthemum and rose mutations induced by X-rays", Am. Soc. Hort. Sci. Proc., pp. 613-620.

Broertjes, 1966, "Mutation breeding of chrysanthemums", Euphytica, 15:156-162.

Dowrick et al., 1966, "The induction of mutations in chrysantheumum using X-ray and gamma radiation", Euphytica, 15:204-210.

*Primary Examiner*—Howard J. Locker

*Attorney, Agent, or Firm*—Foley & Lardner

[57] ABSTRACT

A Chrysanthemum plant named Regal Davis particularly characterized by its flat capitulum form; daisy capitulum type; dark red-purple ray floret color; diameter across face of capitulum of 64 to 70 mm when fully opened when grown as a pinched spray pot mum; photoperiodic flowering response to short days of 55 to 60; plant height, with 15 to 16 long days after sticking unrooted cuttings, and with 2 applications of 2500 ppm B-9 SP, ranges from 20 to 25 cm when gown as a pinched pot mum with 4 cuttings in a 15 cm pot; branching pattern is spreading, each plant having 4 to 6 laterals after pinch; and recommended as a spray pot mum.

1 Drawing Sheet

The present invention comprises a new and distinct cultivar of Chrysanthemum, botanically known as *Dendranthema grandiflora,* and referred to by the cultivar name Regal Davis.

Regal Davis, identified as 4180 (84-382F03), is a product of a mutation induction program. Regal Davis was discovered and selected by Cornelis P. VandenBerg on Jun. 1, 1990 in a controlled environment in Salinas, Calif., in comparative flower trials of selections of radiation sports originating from irradiation of the cultivar identified as Davis, disclosed in U.S. Plant Pat. No. 7,325 and described as a spray pot mum with a flat capitulum form; daisy capitulum type; red purple ray floret color; diameter across face of capitulum of 64 to 70 mm when fully opened; flowering response period of 51 to 63 days after start of short days; plant height of 18 to 28 cm with 2 to 3 applications of 2500 ppm B-9 SP when grown as a pinched pot mum in a 15 cm pot; and spreading and prolific branching pattern, with 4 to 6 laterals after pinch.

One selection in these comparative flower trials was identified by the code number 4059, which was selected in October 1989 as one flowering plant within a flowering block established as rooted cuttings from stock plants of Davis which has been exposed as unrooted cuttings to an X-ray source of 2000 rads in Fort Myers, Fla., on Mar. 30, 1989. Repeated flowerings of code 4059 showed a mixture of plants with different ray floret color. One plant with a very dark purple ray floret color was selected on Jun. 1, 1990 and given the code number 4180 (84-382F03), and subsequently the cultivar name Regal Davis.

The irradiation program resulting in code 4059 and ultimately in Regal Davis had as its primary objective the expansion of color ranges of the parent cultivar Davis. The irradiation program comprised irradiating cuttings of the parent cultivar at irradiation levels of 1500, 1750 and 2000 rads. A total of 1466 cuttings harvested from a total of 225 irradiated plants were planted on Jul. 31, Jul. 24 and Jul. 10, 1989. Of these, 27 initial selections were made, which selections were then revegetated and reflowered. Four consecutive flowerings resulted in discarding 21 of the original 27 selections on Jul. 9, 1990. Three selections were retained and three selections were reselected as possible introductions. Reselections were made because of the fact that the flowering plants consisted of more than one color, as described for 4059. Of these 6 selections, 4 will be commercially introduced as Regal Davis, Coral Davis, Orange Davis and Light Davis, the last three of which are disclosed in pending plant patent applications of applicant.

The first act of asexual reproduction of Regal Davis was accomplished when vegetative cuttings were taken from the initial selection in December 1989 in a controlled environment in Salinas, Calif., by technicians working under the supervision of Cornelis P. VandenBerg. Regal Davis was reselected from the original selection on Jun. 1, 1990. The first act of asexual reproduction of the reselection was assomplished when vegetative cuttings were taken from this reselection in August, 1990, in a controlled environment in Salinas, Calif., by technicians working under the supervision of the inventor.

Horticultural examination of controlled flowerings of successive plantings has shown that the unique combination of characteristics as herein disclosed for Regal Davis are firmly fixed and are retained through successive generations of asexual reproduction.

Regal Davis has not been observed under all possible environmental conditions. The phenotype may vary significantly with variations in environment such as temperature, light intensity and daylength.

The following observations, measurements and comparisons describe plants grown in Salinas, Calif., under green house conditions which approximate those generally used in commercial greenhouse practice.

The following traits have been repeatedly observed and are determined to be basic characteristics of Regal Davis, which, in combination, distinguish this Chrysanthemum as a new and distinct cultivar:

1. Flat capitulum form.
2. Daisy capitulum type.
3. Dark red-purple ray floret color.
4. Diameter across face of capitulum of 64 to 70 mm when fully opened, when grown as a pinched spray pot mum.
5. Photoperiodic flowering response to short days of 55 to 60 days.
6. Plant height, with 15 to 16 long days after sticking unrooted cuttings, and with 2 applications of 2500 ppm B-9 SP, ranges from 20 to 25 cm when grown as a pinched pot mum with 4 cuttings in a 15 cm pot.
7. Branching pattern is spreading, each plant having 4 to 6 laterals after pinch.
8. Recommended as a spray pot mum.

The accompanying color photographic drawing is a top perspective view of potted plants of Regal Davis, with 4 cuttings in a 15 cm pot, with the colors being as nearly true as possible with illustrations of this type.

Of the commercial cultivars known to the inventor, the most similar in comparison to Regal Davis is the parent cultivar Davis. Most traits of Regal Davis are similar to thise of Davis, except for the ray floret color, which is significantly darker than the ray floret color of Davis, and the flowering response time to short days, which is 2 to 4 days slower when compared with the flowering response time to short days of Davis. In several comparative flowering trials Regal Davis also has shown slightly less vigor than Davis. When comparing the description of Regal Davis with Davis, it is evident that Davis has a wider range of flowering response and plant height than Regal Davis. The reason for this is that the description of Davis is based on evaluations over a 2 year time period, while the description of Regal Davis is based on 4 flowerings in a 3 month period.

In the following description color references are made to The Royal Horticultural Society Colour Chart. The color values were determined on plant material grown as a pinched spray pot mum in Salinas, Calif. on Apr. 1, 1991.

Classification:

*Botanical.*—*Dendranthema grandiflora* cv Regal Davis.

*Commercial.*—Flat daisy spray pot mum.

INFLORESCENCE

A. Capitulum:

*Form.*—Flat.

*Type.*—Daisy.

*Diameter across face.*—64 to 70 mm when fully opened.

B. Corolla of Ray Florets:

*Color (general tonality from a distance of three meters) ).*—Dark red-purple

*Color (upper surface).*—71B.

*Color (under surface).*—70B to 70C.

*Shape.*—Straight, oblong, slightly ribbed.

C. Corolla of Disc Floriets:

*Color (mature).*—9A.

*Color (immature).*—144B.

D. Reproductive Organs:

*Androecium.*—Present on disc florets only; no pollen.

*Gynoecium.*—Present on both ray and disc florets.

PLANT

A. General Appearance:

*Height.*—20 to 25 cm when grown as a pinched pot mum with 15 to 16 long days prior to start of short days, with 2 applications of 2500 ppm B-9 SP.

*Branching pattern.*—Spreading and prolific, with 4 to 6 lateral after pinch.

B. Foliage:

*Color (upper surface).*—147A.

*color (under surface).*—147B.

*Shape.*—Deeply lobed and serrated.

I claim:

1. A new and distinct Chrysanthemum plant named Regal Davis, as described and illustrated.

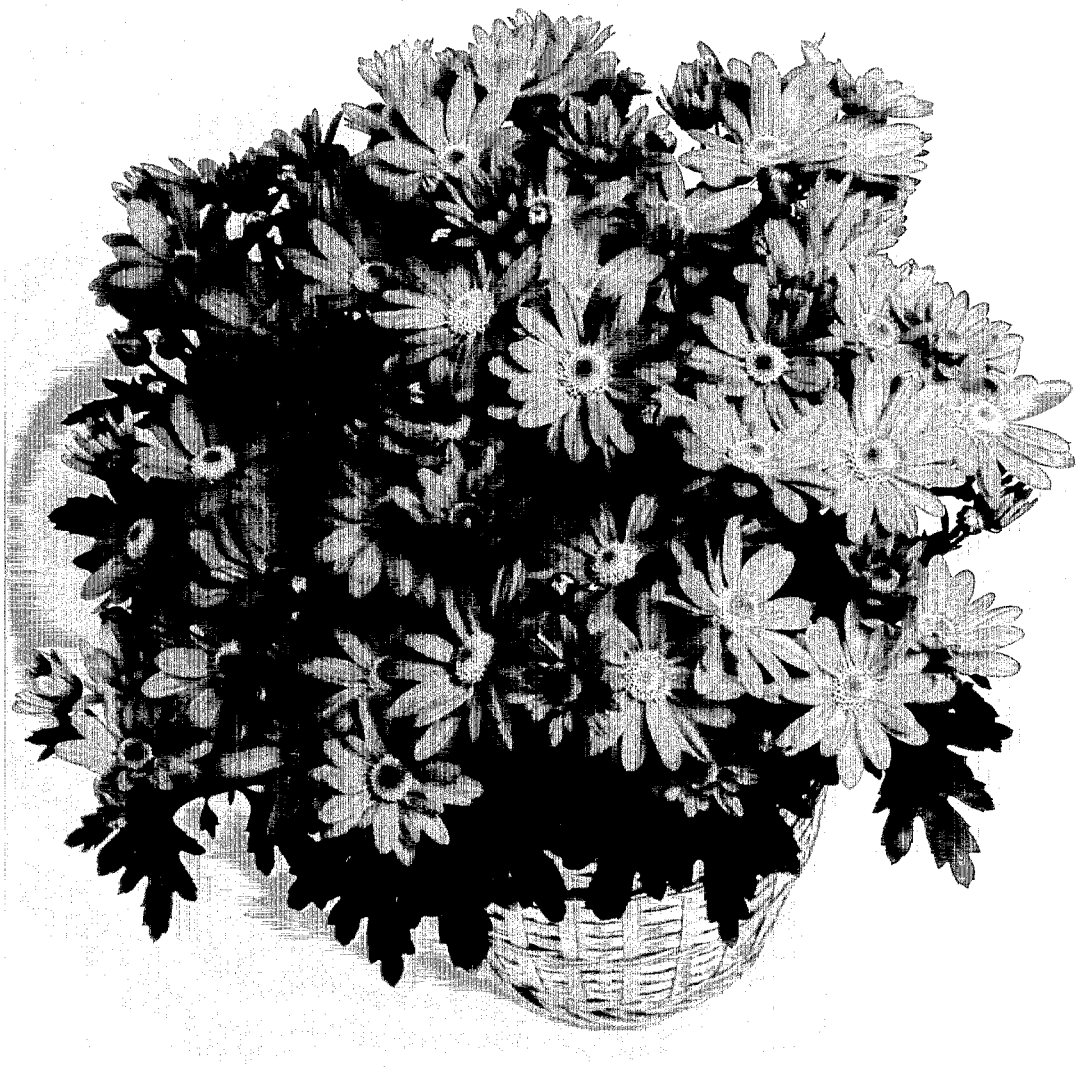

* * * * *